United States Patent [19]
Davies

[11] Patent Number: 6,015,799
[45] Date of Patent: *Jan. 18, 2000

[54] DEXTRIN SULFATES AND ANTI HIV-1 AGENTS AND COMPOSITION THEREOF

[75] Inventor: Donald Selwyn Davies, Beaconsfield, United Kingdom

[73] Assignee: M.L. Laboratories PLC, Liverpool, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/410,067

[22] Filed: Mar. 24, 1995

Related U.S. Application Data

[63] Continuation of application No. 08/030,227, filed as application No. PCT/GB91/01628, Sep. 23, 1991, Pat. No. 5,439,892.

[30] Foreign Application Priority Data

Sep. 25, 1990 [GB] United Kingdom .................... 9020861

[51] Int. Cl.[7] ..................................................... A61K 31/70
[52] U.S. Cl. ................................. 514/58; 514/54; 514/60; 514/885; 536/103
[58] Field of Search ......................... 514/58, 885; 536/54, 536/103; 579/60

[56] References Cited

U.S. PATENT DOCUMENTS

| | | | |
|---|---|---|---|
| 2,967,178 | 1/1961 | Kerr et al. ................................. | 536/54 |
| 4,840,941 | 6/1989 | Ueno et al. ................................ | 514/59 |
| 5,153,181 | 10/1992 | Diringer et al. .......................... | 514/54 |
| 5,221,669 | 6/1993 | Anand et al. .............................. | 514/58 |
| 5,258,175 | 11/1993 | Davies ..................................... | 424/422 |

FOREIGN PATENT DOCUMENTS

WO88/00211 1/1988 WIPO .

*Primary Examiner*—Elli Peselev
*Attorney, Agent, or Firm*—Rodman & Rodman

[57] ABSTRACT

This invention provides an agent against HIV-1 and related viruses, the agent being or including dextrin sulphate containing at most two sulphate groups per glucose unit. The invention also provides a composition containing such an agent, and the use of the agent or composition against HIV-1 and related viruses. By restricting the degree of substitution of the dextrin sulphate to a maximum of 2, the invention makes it possible to produce a dextrin sulphate having adequate anti-HIV activity whilst maintaining toxicity within acceptable limits.

13 Claims, No Drawings

DEXTRIN SULFATES AND ANTI HIV-1 AGENTS AND COMPOSITION THEREOF

This appln is a 371 of PCT/GB91/01628, filed Sep. 23,1991 and this is a continuation of application Ser. no. 08/030,227 filed Jun. 22, 1993, now U.S. Pat. No. 5,439,892.

This invention relates to pharmaceutically active materials and compositions and in particular to the use of such materials and compositions as agents against human immunodeficiency virus type I (HIV-1) and related viruses.

It is known that some sulphated polysaccharides have anti-HIV activity; see, for example, European Patent Specification No. 240,098. This specification discloses highly sulphated oligosaccharides obtained by sulphation of dextrins of relatively low molecular weight.

According to the present invention there is provided an agent against HIV-1 and related viruses, the agent being or including dextrin sulphate containing at most two sulphate groups per glucose unit. Dextrin is a mixture of polymers of glucose and the glucose units may be substituted in one or more of the 2, 3 and 6 positions by sulphate groups.

The present invention also provides compositions containing such an agent. In addition, the invention provides the use of such an agent or compositions against HIV-1 and related viruses.

A dextrin sulphate of use in the present invention may have up to two sulphate groups per glucose unit and preferred dextrin sulphates are those having about 1, or between 0.5 and 1.5, preferably up to 1.2, sulphate groups per glucose unit. More preferably, the agent is the 2- or 6-sulphate of dextrin or a mixture thereof.

We have found that dextrin 2-sulphate has about the same activity against the HIV-1 virus as the dextrin 6-sulphate. However, the latter has a greater anti-coagulant activity and for this reason dextrin 2-sulphate is a particularly preferred agent.

We have also found that dextrin 3-sulphates have relatively poor anti-HIV activity, by comparison with dextrin 2- and 6-sulphates. It follows that for a given sulphate content the anti-HIV activity of a dextrin sulphate is inversely related to the proportion of 3-sulphation. Under most reaction conditions the 3-OH group of the glucose residue in a dextrin has been found to be less reactive than the 2-OH and 6-OH groups. Therefore, enhanced anti-HIV activity per sulphate group can be achieved by keeping the degree of sulphation relatively low, thereby reducing the extent of 3-sulphation.

However, in selecting a particular sulphated dextrin as an anti-HIV agent conflicting factors are encountered. Thus, generally speaking:

1. For a given sulphate content:
   (a) the toxicity increases with increasing molecular weight, and
   (b) the anti-HIV activity increases with increasing molecular weight.
2. For a given molecular weight:
   (a) the toxicity increases with increasing sulphate content, and
   (b) the anti-HIV activity increases with increasing sulphate content.

It has seemed that dextrin sulphates might in fact be unusable in practice as anti-HIV agents because satisfactory anti-HIV activity appeared to go hand-in-hand with unacceptable toxicity, either because the molecular weight was too high or because the sulphate content was too high.

By restricting the degree of substitution to a maximum of 2 the present invention makes it possible to produce a dextrin sulphate having adequate anti-HIV activity while keeping toxicity within acceptable limits. With a relatively low degree of substitution the proportion of 3-sulphation can be kept low, so that the toxicity imported into the dextrin sulphate by 3-substitution is avoided. If a dextrin is fully substituted, i.e. to give the 2,3,6-sulphate, one-third of the sulphate groups are 3-sulphate groups, which give rise to additional toxicity out of all proportion to the extent to which they enhance the anti-HIV activity. The extent to which 3-sulphation occurs when the degree of substitution is kept below 2 varies with the nature of the sulphation process, but is normally substantially less than that of 2-sulphation or 6-sulphation. Presently available analytical techniques do not easily permit accurate analysis of the extent of sulphation at the three available sites, but an examination of the n.m.r. spectrum of a dextrin sulphate gives a sufficient indication of this for practical purposes. The total sulphate content can of course be evaluated by conventional analytical methods, normally by determining the sulphur content.

The molecular weight of dextrin sulphate of use in this invention may vary over a wide range. By way of example, dextrin sulphate of use in the present invention may have a weight average molecular weight of from 15,000 to 25,000 as determined on the dextrin used to prepare the dextrin sulphate. The technique used to determine molecular weight of the dextrin is high-pressure liquid chromatography using chromatographic columns calibrated with dextran standards, as designated by Alsop et al, J Chromatography 246, 227–240 (1989).

Dextrin sulphate can be prepared by first hydrolysing starch to produce dextrin which may then be sulphated to produce dextrin sulphate. For example, use of a trimethylamine/sulphur trioxide complex in aqueous alkaline medium gives predominantly the 2-sulphate. Treatment of dextrin with cyclamic acid in dimethylformamide gives the 6-sulphate. The 3-sulphate may be made by first acetylating dextrin, then sulphating it with trimethylamine/sulphur trioxide complex in dimethylformamide and finally removing the acetyl groups with aqueous sodium hydroxide.

It is preferred to use dextrin sulphate in which there is a low proportion of low molecular weight material. As has been mentioned above, dextrin is made by hydrolysis of starch, typically by treatment of various starches with dilute acids or with hydrolytic enzyme. Such methods produce glucose polymers with a wide range of polymerisation. The degree of polvmerisation (D.P.) varies from one or two up to comparatively high numbers. The direct hydrolysis product of starch might contain up to 60% by weight of material having a D.P. less than 12. In a preferred aspect of the present invention, the dextrin derivative contains a relatively high proportion of glucose polymers of D.P. greater than 12. Preferably, the dextrin derivative contains at least 50% by weight of glucose polymers of D.P. greater than 12.

More preferably, the dextrin derivative contains less than 10% by weight of glucose polymers having a D.P. less than 12. Most preferably, the dextrin derivative contains less than 5% by weight of glucose polymers having a D.P. less than 12. Such dextrin derivatives are prepared from dextrin which has been fractionated to remove dextrin with a low D.P. Known fractionation techniques may be used, including solvent precipitation and membrane fractionation.

A method of preparing a glucose polymer mixture is described in GB 2132914 and a method for preparation of a glucose polymer mixture with a relatively low proportion of low D.P. glucose polymers is described in Example 2 of GB 2154469. This mixture has a weight average molecular weight of 23,700 and contains 91.9% of polymers having a degree of polymerisation greater than 12 and 7.9% of polymers having a degree of polymerisation from 2 to 10.

It is also preferred that the dextrin derivative contains little or no material with a high molecular weight. More preferably, the dextrin derivative contains little or no material with a molecular weight greater than 40,000.

Dextrin sulphate is a particularly effective agent against HIV-1 and related viruses. Although the mechanism of its action is not understood, it may be that dextrin sulphate acts to block the attachment of the virus to cells. It appears that because of its particular somewhat globular conformation, dextrin sulphate provides a carrier of relatively closely packed sulphate groups which can particularly effectively prevent attachment of the virus to the cell and hence entry of the virus.

Dextrin sulphate may be effective in relatively low concentrations. Furthermore, the above-mentioned globular conformation of dextrin sulphate appears to allow the material to be effective against HIV-1 and related viruses even with a relatively low degree of sulphation. For instance, a degree of sulphation as low as one sulphate group per glucose unit, or even lower, is found to be effective at relatively low concentrations. This has the advantage that the amount of sulphation can be kept to such a low level as to avoid the side effects and toxicity which might otherwise be experienced with highly sulphated materials.

Dextrin sulphate can be taken enterally (including orally), but preferably is administered parenterally, for instance, intravenously. However, administration via the peritoneum may be more effective than intravenous administration in that it results in entry of at least some of the dextrin sulphate directly into the lymphatic system, within which system viral replication may be extensive.

The invention also provides a composition comprising an agent as described above as being in accordance with the invention, together with an inert carrier or diluent.

Further, the invention provides the use of the agent or composition of the invention against HIV-1 and related viruses, the agent or composition preferably being administered intra-peritoneally. The agent of the invention is preferably adapted for intraperitoneal administration.

The invention additionally provides an agent as described above as being in accordance with the invention, for use in the manufacture of a pharmaceutical composition for the treatment of HIV-1 and related viruses.

Further, the invention provides a method of treatment of a human or animal subject carrying the HIV-1 virus or a related virus, comprising administering to the subject a pharmaceutically effective amount of the agent of the invention.

The following examples illustrate methods for the preparation of dextrin sulphate:

EXAMPLE 1

Preparation of Dextrin 3-sulphate 16.2 g of the aforementioned dextrin of Example 2 of GB 2,154,469 in dimethylformamide (150 mL) was stirred and heated until dissolved, then cooled to ambient temperature. Acetic anhydride (23 mL, 0.24 mole) was added slowly with stirring. A transient precipitation occurred and when this had redissolved, triethylamine (25 mL, 0.18 mole) was added and the mixture stirred for 2 days. The solution was then poured in a thin stream with stirring into water (700 mL), the precipitate was filtered off, washed with water and dried to give 23 g of white powder.

The acetylated dextrin (12.3 g) in dimethylformamide (75 mL) was stirred until dissolved then trimethylamine sulphur trioxide complex (15 g) was added and the mixture was stirred at ambient temperature overnight. Further trimethylamine sulphur trioxide (10 g) was added and the mixture heated at 60° C. for 3 hours. The solution was cooled and poured into acetone (500 mL) to give a sticky residue. The supernatant was decanted and the residue kneaded with fresh acetone (50 mL) and then the supernatant decanted. The residue was dissolved in water (150 mL) and the remaining acetone stripped off under vacuum. A solution of NaOH (5 g) in water (10 mL) was added giving trimethylamine gas. The strongly basic solution was stored for 2 h, dialysed against water for 4 days and freeze dried, to give 10.2 g. The I.R. spectrum showed peaks for acetate (1750 $CM^1$) and sulphate (1240 $Cm^{-1}$).

The product (10 g) was redissolved in water (150 mL) and NaOH (1 g) in water added and the mixture stirred 3 h at ambient temperature. The solution was poured into ethanol (300 mL), the supernatant was decanted and the sticky residue kneaded with fresh ethanol (150 mL) to give a solid. The solid was filtered off, washed with methanol and dried to a brown powder. The powder was dissolved in water (200 mL) and decolourising charcoal (5 g) added. The solution was warmed then filtered twice and freeze-dried to give 7.2 g, sulphate, 46.9%.

EXAMPLE 2

Preparation of Dextrin 6-sulphate 10 g of the same dextrin as in Example 1 in dimethylformamide (100 mL) was heated and stirred at 78° C. When the dextrin had all dissolved cyclamic acid (22.5 g) was added and the reaction continued for 1.5 h. A solution of NaOH (5 g) in water (5 mL) and ethanol (50 mL) was added and the mixture poured into diethyl ether (400 mL). The solid was filtered off, washed with ether and air dried. The solid was dissolved in water (100 mL), sodium acetate (50 g) added and the solution dialysed against water for 4 days then freeze dried to give 15.4 g, sulphate 47.2%.

EXAMPLE 3

Preparation of Dextrin 2-sulphate 40 g of the same dextrin as in Example 1 in distilled water (150 ml) were stirred in a round bottomed flask at 30° C. When the dextrin had all dissolved trimethylamine sulphur trioxide (51 g) were added to the solution. The reaction mix was stirred for thirty minutes. Sodium hydroxide (62.5 ml @ 40% w/v) was added dropwise to the reaction mix over a period of one hour. The reaction mix was then stirred for a further two hours and filtered under vacuum. The resultant solution was dialysed for one day against tap water and one day against distilled water. The dialysed solution was then concentrated by evaporation at reduced pressure. The concentrated solution contained 30 g of dissolved solids at 36% w/w (wrt dry solids) sulphate.

The products of Examples 1, 2 and 3 have been identified as the 3-,6- and 2-sulphates respectively by examination of their n.m.r. spectra.

The 13C n.m.r. spectrum of the original dextrin shows six lines. These can mostly be assigned, by reference to standard compounds, as: 100.3, C-1; 77.6, C-4; 73.9, C-3; 72.2 and 71.8, C2 and C-5; 61.1, C-6.

The n.m.r. spectra of both the 3- and 6-sulphates of glucose have been reported (S. Honda, Y. Yuki and K. Tahiura, Carbohydrate Research (1973) Volume 28, pages 130 to 150) and compared to the free sugars. Thus, 3-O-sulphation was observed to cause 8.5 or 9.5 ppm downfield shift for C-3, a 1.1 ppm upfield shift for C-2 and 2.2. ppm upfield shift for C-4, but little change for other positions. For 6-O-sulphation, a downfield shift of 6.2 ppm was observed for C-6 and upfield shifts of 1.7 ppm for C-5 and 0.3 ppm for C-4, with little change in the other positions.

The n.m.r. spectrum of the product of Example 1 shows a strong signal at 61.1 ppm, characteristic of unmodified C-6-OH. Prominent new signals have appeared at 82.2 and 82.5 ppm. These are close to the chemical shift of 82.7 ppm reported for C-3 in D-glucose-3-sulphate and are therefore assigned to dextrin-3-sulphate. This assignment is supported by the virtual disappearance of the signal at 77.6 ppm in the original dextrin for C-4. Substitution at 0-3 is expected to cause an upfield shift of the signal for C-4, taking it under the envelope of other signals. New peaks at 70.2 and 70.8 ppm are attributed to C-2 in a 3-sulphate by upfield shift from the original position at 72.2 or 71.8 ppm. The C-1 region shows six closely spaced lines between 100.1 and 98.3 ppm slightly upfield from that in the original dextrin. From this data it appears that the product of Example 1 is sulphated almost entirely in the 3-position.

The n.m.r. spectrum of the product of Example 2 shows that the original C-6 peak at 61.1 ppm has greatly diminished and new peaks have appeared at 67.5 ppm and 69.3 ppm, for C-6-O-sulphate (6.4 ppm downfield shift) and for C-5 adjacent to 6-O-sulphate (2.5 or 2.9 upfield shift) respectively. This data indicates that the product of Example 2 is substituted primarily in the 6-position.

The n.m.r. spectrum of the product of Example 3, in comparison with that of the original dextrin, shows a major signal for unsubstituted C-6-OH at 61.1 ppm, unperturbed C-4 signal at 78.1 ppm, indicating free 3-OH and the major C-1 signal moved upfield to 99.8 ppm from its original position at 100.3 ppm. From this data it appears that the product of Example 3 is substituted primarily in the 2-position.

In the following Example, the effectiveness of dextrin sulphate against HIV-1 was tested and compared with other materials, namely, dextran, dextran sulphate and zidovidine (AZT).

EXAMPLE 4

Effectiveness of Dextrin 2-sulphate Against HIV-1

The dextran sulphate had a molecular weight of 500,000 and was obtained from the Sigma Chemical Company and further purified by column chromatography. The dextran had a molecular weight of 90,000. The dextrin 2-sulphate (referred to as NBSD24 and prepared as described in Example 3 above) contains one sulphate group per glucose unit as indicated by infra-red analysis.

Elemental analysis indicated 12.7% sulphur equivalent to 1.1 sulphate groups per glucose unit.

Normal human peripheral blood lymphocytes (PBL) were fractionated on Ficoll-Hypaaue (Pharrmacia Chemicals, Uppsala, Sweden) from venous blood collected in preservative-free heparin. They were mitogenetically stimulated with phytohaemaglutinin (PHA) (1 ug/ml) for 3 days and maintained in the medium RPMI 1640 supplemented by 20% foetal calf serum (FCS)+interleukin-2 (IL2) (50–100 g u/ml).

The human T-leukamic cell line C8166 was grown in RPMI 1640 with 10% FCS.

Various strains of HIV-1 (RF. IIIB, CBL-4, Z84 and Z129) were produced in chronically infected H9 cells. A five-fold excess of uninfected H9 cells was added to the culture five days prior to harvesting the supernatant which is clarified by centrifugation and stored in liquid nitrogen. Induction of cytopathic effects on CD4+ C8166 by HIV was assayed by multi-nucleated giant cell formation (syncytia).

The following table illustrates the sensitivity of HIV-1 to the two sulphated materials, the non-sulphated dextran and AZT in the C8166 infectivity assay, determined by syncytial induction:

| Drug | Concentration (ug/ml) | | | | | |
|---|---|---|---|---|---|---|
| | 0 | 0.1 | 1.0 | 10 | 100 | 200 |
| NBSD24 | −6 | ND | −4 | −2 | −2 | |
| Dextran Sulphate | −6 | −6 | −6 | −3 | cell death | |
| Dextran | −6 | −6 | −6 | −6 | | |
| AZT | −6 | −4 | −3.5 | −3 | −3 | |

HIV-1 (RF) was titrated in 10-fold dilutions onto C8166 cells in the presence of varying concentrations of drug. Final dilutions of the virus at which syncytia are produced are shown. The figures in the table represent the logarithm to the base 10 of the figure actually determined. For instance, a figure of −6 in the table represents a determined result of $10^{-6}$. ND means that a result was "not determined" for the particular drug concentration. At a concentration 10 ug/ml, dextrin 2-sulphate and dextran sulphate each reduced the infectious titre by 3 logs, which compares favourably with the 3 log reduction effected by AZT. Dextran was ineffective against HIV replication. At 1 ug/ml, inhibition occurs with dextrin sulphate (2 logs) and AZT (2.5 logs). These results were confirmed by a colorimetric assay as shown in the following table:

| Drug | Concentration (ug/ml) | | | |
|---|---|---|---|---|
| | 0 | 0.1 | 1.0 | 10 |
| NBST24 | + | + | − | − |
| Dextran Sulphate | + | + | − | − |
| Dextran | + | + | + | − |
| AZT | + | − | − | − |

Inhibition of HIV-1 (RF), assayed by live cell (C8166) reduction of MTT, was estimated visually and is represented by a minus.

The following table illustrates the decrease in infectivity titre (log units) in C8166 cells of HIV-1:

| Drug | (ug/ml) | RF | IIIB | CBL-4 |
|---|---|---|---|---|
| NBSD24 | 10 | 5 | 3 | 0 |
| | 50 | 6 | 5 | 4 |
| Dextran Sulphate | 10 | 3 | 2 | 0 |
| | 50 | 1 | 0 | 0 |
| AZT | 10 | 3 | 4 | 4 |
| | 50 | 3 | 4 | 4 |

These results indicate that dextrin 2-sulphate inhibits syncytial induction on C8166 cells with greater effect than either AZT or dextran sulphate.

EXAMPLE 5

Toxicity of Dextrin 2-sulphate

The relative toxicities of the materials tested in example 4 were evaluated by reference to cell viability in the presence of the drugs as measured by the relative uptake of [$^3$H]-thymidine. Human PBL ($10^6$ cells/well) in 96 microtitre plates was stimulated with PHA in the presence of increasing concentration of drug for 3 days. Following a 5 hour probe with [$^3$H]-thymidine (0.5 uCi/well), the cells were harvested and counted. The results shown represent the mean of quadruplicate experiments and are presented as the percentage incorporation of [$^3$H]-thymidine in the presence of drug, compared to control experiments without drug. The results are given below:

| Thymidine uptake (% of control with no drug) | | | | | | | |
|---|---|---|---|---|---|---|---|
| Concentration (ug/ml) | 5 | 10 | 25 | 50 | 71 | 100 | 200 |
| AZT | 20 | 15 | 5 | 2 | 1 | 1 | 0 |
| NSBD24 | 65 | 120 | 105 | 90 | 90 | 85 | 78 |
| Dextran | 95 | 97 | 80 | 70 | 67 | 78 | 60 |
| Dextran sulphate | 105 | 113 | 110 | 66 | 57 | 30 | 15 |

The dextran had a molecular weight of 90,000 and the dextran sulphate had a molecular weight of 500,000. In practice, there would be a need to use the particular drug in a concentration of around 200 ug/ml. It can be seen that, at this sort of concentration, AZT is very highly toxic and dextran sulphate is also highly toxic. By comparison, dextrin 2-sulphate is somewhat less toxic than the non-sulphated material dextran.

EXAMPLE 6

Comparison of the Effectiveness of Dextrin 2-, 3- and 6-sulphates 50 ul samples of dextran sulphate and of the 2-, 3- and 6-sulphate derivatives of dextrin of Examples 3, 1 and 2 respectively were pre-incubated at 37° C. onto duplicate cultures of $4 \times 10^5$ M8166 JH11 cells per ml (50 ul) at final concentrations of 50, 5, 0.5 and 0.05 ug/ul for one hour. 50 ul of $10^3$ TCID (IIIb, RF, CBL20) or $10^2$ TCID (RUT) was added and cultures were incubated until control cultures (absence of any effector) showed 90%+syncytia (2–3 days). The inhibitory concentration was taken to be the minimum concentration at which syncytia formation was found to be <10% that of controls at the end point. The results are shown in the following table:

| | IIIb | RF | RUT | CBL2O |
|---|---|---|---|---|
| Dextran sulphate | 5 | 50 | 50 | 50 |
| Dextrin 2-sulphate | 5 | 5 | 5 | 50 |
| Dextrin 3-sulphate | 50 | 5 | 50 | >50 |
| Dextrin 6-sulphate | 5 | 5 | 50 | >50 |

The dextran sulphate had a molecular weight of 8,000. These results indicate the overall greater effectiveness of the 2- and 6-sulphates of dextrin compared with the dextran sulphate and dextrin 3-sulphate (the latter being more effective than dextran sulphate against RF).

EXAMPLE 7

Comparison of the Anti-coagulant Activity of the Dextrin Sulphate

The materials to be tested were each dissolved in veronal buffer to a concentration of 1 mg/ml=1000 ug/ml and a further dilution of 100 ug/ml was made by a 1:10 dilution in veronal buffer. Pooled normal plasma (1 ml) was then placed into each of nine plastic tubes. The solutions containing the materials to be tested were then added to the plasma to achieve a range of final concentrations from 1–300 ug/ml, in each case the volume being made up to 1.5 ml with veronal buffer. The resultant mixtures were incubated at 37° C. for 30 minutes, following which two 0.2 ml aliquots were extracted from each sample into glass tubes (Samples A and B), and 0.1 ml 7 U Bovine Thrombin was added and clot formation timed. The following results were obtained:

| | | Time (secs) | | | | |
|---|---|---|---|---|---|---|
| Concn (ug/ul) | Sample | Dextran sulphate | Dextrin 2-sulphate | Dextrin 6-sulphate | Dextrin 3-sulphate | Dextran 2,3,6-sulphate |
| 0 | A | 17 | 17 | 17 | 17 | 17 |
| | B | 17 | 16 | 17 | 17 | 17 |
| 1 | A | 17 | 20 | 19 | 17 | 25 |
| | B | 17 | 20 | 19 | 18 | 25 |
| 5 | A | 21 | 32 | 47 | 22 | 42 |
| | B | 22 | 33 | 48 | 24 | 46 |
| 10 | A | 27 | 53 | 91 | 30 | >180 |
| | B | 28 | 55 | 92 | 30 | >180 |
| 20 | A | 31 | 83 | 162 | 40 | >180 |
| | B | 33 | 83 | 166 | 41 | >180 |
| 50 | A | >180 | 123 | >180 | 62 | >180 |
| | B | >180 | 120 | >180 | 64 | >180 |
| 100 | A | >180 | 150 | >180 | 85 | >180 |
| | B | >180 | 150 | >180 | 87 | >180 |
| 200 | A | >180 | >180 | >180 | 110 | >180 |
| | B | >180 | >180 | >180 | 114 | >180 |
| 300 | A | >180 | >180 | >180 | >180 | >180 |
| | B | >180 | >180 | >180 | >180 | >180 |

These results illustrate that the least anti-coagulant dextrin materials are the 2- and 3-sulphates.

I claim:

1. A method of treatment of a human or animal subject against the HIV-1 virus or an HIV-1 related virus, comprising administering to the subject a pharmaceutically effective amount of an agent against HIV-1 and HIV-1 related viruses, comprising dextrin sulphate containing at most two sulphate groups per glucose unit.

2. The method of claim 1, wherein the agent comprises about 0.5 to 1.5 sulphate groups per glucose unit.

3. The method of claim 2, wherein the agent comprises up to about 1.2 sulphate groups per glucose unit.

4. The method of claim 1, wherein the dextrin sulphate is selected from the group consisting of dextrin 2-sulphate, dextrin 6-sulphate and mixtures thereof.

5. The method of claim 1, wherein the dextrin sulphate contains at least 50% by weight of glucose polymers of D.P. greater than 12.

6. The method of claim 1, wherein the dextrin sulphate contains less than 10% by weight of glucose polymers having a D.P. less than 12.

7. The method of claim 1, wherein the dextrin sulphate contains less than 5% by weight of glucose polymers having a D.P. less than 12.

8. The method of claim 1, wherein the weight average molecular weight of the dextrin sulphate is at least 15,000.

9. The method of claim 1, wherein the dextrin sulphate is substantially free from polymers of molecular weight greater than 40,000.

10. The method of claim 1, wherein the agent is formulated with an inert carrier or diluent.

11. The method of claim 1, wherein the agent is administered intraperitoneally.

12. The method of claim 1, wherein the weight average molecular weight of the dextrin oulphate is from about 15,000 to 25,000.

13. The method of claim 1, wherein the dextrin sulphate has a globular conformation.

* * * * *